United States Patent
Ameer et al.

(10) Patent No.: US 9,211,363 B2
(45) Date of Patent: Dec. 15, 2015

(54) CONTROLLED AND LOCALIZED RELEASE OF RETINOIDS TO IMPROVE NEOINTIMAL HYPERPLASIA

(71) Applicant: VesselTek BioMedical LLC, Chicago, IL (US)

(72) Inventors: Guillermo A. Ameer, Chicago, IL (US); Melina Kibbe, Chicago, IL (US); Antonio Webb, Evanston, IL (US)

(73) Assignee: VesselTek BioMedical LLC, Chicago, IL (US)

( * ) Notice: Subject to any disclaimer, the term of this patent is extended or adjusted under 35 U.S.C. 154(b) by 0 days.

(21) Appl. No.: 14/546,033

(22) Filed: Nov. 18, 2014

(65) Prior Publication Data

US 2015/0071984 A1 Mar. 12, 2015

Related U.S. Application Data

(63) Continuation of application No. 12/497,187, filed on Jul. 2, 2009, now abandoned.

(60) Provisional application No. 61/077,949, filed on Jul. 3, 2008.

(51) Int. Cl.
| | |
|---|---|
| *A61F 2/00* | (2006.01) |
| *A61L 33/04* | (2006.01) |
| *A61L 27/34* | (2006.01) |
| *A61L 27/50* | (2006.01) |
| *A61L 27/54* | (2006.01) |
| *A61L 31/10* | (2006.01) |
| *A61L 31/16* | (2006.01) |
| *A61L 31/08* | (2006.01) |

(52) U.S. Cl.
CPC .............. *A61L 33/04* (2013.01); *A61L 27/34* (2013.01); *A61L 27/507* (2013.01); *A61L 27/54* (2013.01); *A61L 31/08* (2013.01); *A61L 31/10* (2013.01); *A61L 31/16* (2013.01); *A61L 2300/416* (2013.01); *A61L 2300/428* (2013.01); *A61L 2300/602* (2013.01); *A61L 2300/606* (2013.01); *A61L 2300/626* (2013.01); *A61L 2420/06* (2013.01); *A61L 2430/36* (2013.01)

(58) Field of Classification Search
CPC ....... A61L 27/34; A61L 27/507; A61L 27/54; A61L 31/10; A61L 31/16; A61L 2300/416; A61L 2300/428; A61L 2430/36; A61L 31/08; A61L 33/04; A61L 2300/602; A61L 2300/606; A61L 2300/626; A61L 2420/06
See application file for complete search history.

(56) References Cited

U.S. PATENT DOCUMENTS

| 8,404,264 | B2 | 3/2013 | Ameer et al. |
| 2003/0118692 | A1 | 6/2003 | Wang et al. |
| 2004/0199241 | A1* | 10/2004 | Gravett et al. ............... 623/1.13 |
| 2005/0063939 | A1 | 3/2005 | Ameer et al. |
| 2005/0123605 | A1 | 6/2005 | Hunter et al. |
| 2007/0185069 | A1 | 8/2007 | Plum et al. |
| 2007/0208420 | A1 | 9/2007 | Ameer et al. |
| 2009/0047256 | A1* | 2/2009 | Bettinger et al. ............ 424/93.7 |
| 2011/0172785 | A1 | 7/2011 | Wolinsky et al. |

FOREIGN PATENT DOCUMENTS

| CN | 101007187 A | 8/2007 |
| JP | 2002-320629 | 11/2002 |
| JP | 2002320629 | 11/2002 |
| WO | WO 2004/060424 | 7/2004 |
| WO | WO 2005/046747 | 5/2005 |
| WO | WO 2006/078282 | 7/2006 |
| WO | WO 2008/011093 | 1/2008 |

OTHER PUBLICATIONS

DeRose et al ("Retinoic acid suppresses intimal hyperplasia and prevents vessel remodeling following arterial injury," Cardiovascular Surgery Oct. 1999 vol. 7 No. 6).*
Ahanchi, et al., "The Role of Nitric Oxide in the Pathophysiology of Intimal Hyperplasia", *J. Vasc. Surg.*, Jun. 2007, vol. 45(6), pp. A64-A73.
Genis, et al., "Macrophages, myofibroblasts and neointimal hyperplasia after coronary artery injury and repair", Atherosclerosis, Jul. 2002, vol. 163(1), pp. 89-98. (Abstract only).
Gradus-Pizlo, et al., "Local Delivery of Biodegradable Microparticles Containing Colchicine or a Colchicine Analogue: Effects on Restenosis and Implications for Catheter-Based Drug Delivery", Journal of the American College of Cardiology, Nov. 15, 1995, vol. 26(6), pp. 1549-1557.
Gray, et al., "Drug-Coated Balloons for the Prevention of Vascular Restenosis", Circulation 2010, vol. 121, pp. 2672-2680.
Hou, et al., "Intrapericardial Paclitaxel Delivery Inhibits Neointimal Proliferation and Promotes Arterial Enlargement After Porcine Coronary Overstretch", Circulation, 2000, vol. 102, pp. 1575-1581.
Jiang, et al., "Established neointimal hyperplasia in vein grafts expands via TGF-β-mediated progressive fibrosis", *Am. J. Physiol. Heart Circ. Physiol.*, 2009, vol. 297, pp. H1200-H1207.
Milewski, et al., "Effects of local intracoronary paclitaxel delivery using the Remedy transport catheter of neointimal hyperplasia after stent implantation in a porcine model", *Cardiovascular Revascularization Medicine*, 2011, vol. 12, pp. 82-89.

(Continued)

*Primary Examiner* — Suzanne Ziska
(74) *Attorney, Agent, or Firm* — Casimir Jones SC; David Staple

(57) ABSTRACT

Controlled release vascular implants, such as vascular grafts, stents, wraps, and gels comprising a biocompatible polymer and all trans retinoic acid (ATRA), or its derivatives, can be used to treat, prevent, or inhibit thrombosis and/or neointimal hyperplasia which may otherwise be induced by prosthetic implantation. In particular, the implants herein can inhibit smooth muscle cell proliferation, neointimal hyperplasia, and upregulate antithrombotic genes and nitric oxide production in the vasculature. Further, the implants are capable of delivering controlled and predictable localized concentrations of ATRA.

18 Claims, No Drawings

(56) References Cited

OTHER PUBLICATIONS

Oberhoff, et al., "Site-specific delivery of cytostatic agents", *Local Drug Delivery for Coronary Artery Disease*, 2005, pp. 275-280.
Oberhoff, et al., "Local Delivery of Paclitaxel Using the Double-Balloon Perfusion Catheter Before Stenting in the Porcine Coronary Artery", *Catheterization and Cardiovascular Interventions*, 2001, vol. 53, pp. 562-568.
Okoshi, et al., "All-trans-Retinoic Acid Attenuates Radiation-Induced Intestinal Fibrosis in Mice", *J. Surg. Res.*, Nov. 2008, vol. 150(1), pp. 53-59. (Abstract only).
Pakala, et al., "RAR gamma agonists inhibit proliferation of vascular smooth muscle cells", *J. Cardiovasc. Pharmacol.*, 2000, vol. 35(2), pp. 302-308. (Abstract only).
Pearce, et al., "Beneficial Effect of a Short-Acting NO Donor for the Prevention of Neointimal Hyperplasia",*Free Radical Biol Med*, 2008, vol. 44, pp. 73-81.
Tabata, et al., "All-trans retinoic acid modulates radiation-induced proliferation of lung fibroblasts via Il-6/1L-6R system", *Am. J. Physiol Lung Cell Mol Physiol*, 2006, vol. 290, pp. L597-L606.
Varu, et al., "Insulin Enhances the Effect of Nitric Oxide at Inhibiting Neointimal.Hyperplasia in a Rat Model of Type 1 Diabetes", *Am. J. Physiol. Heart Circ. Physiol*, Sep. 2010, vol. 299(3), pp. H772-H779.
Yang, et al., "Novel Citric Acid-Based Biodegradable Elastomers for Tissue Engineering", *Advanced Materials*, Mar. 2004, vol. 16(6), pp. 511-516. (Abstract only).
Yang, et al., "Synthesis and evaluation of poly(diol citrate) biodegradable elastomers", *Biomaterials*, Mar. 2006, vol. 27(9), pp. 1889-1898. (Abstract only).
Achan, et al., "all-*trans*-Retinoic Acid Increases Nitric Oxide Synthesis by Endothelial Cells", *Circ. Res.*, vol. 90, pp. 764-769, (2002).
Batchelor, et al., "More Lipophilic Dialkyldiamine-Based Diazeniumdiolates: Synthesis, Characterization, and Application in Preparing Thromboresistant Nitric Oxide Release Polymeric Coatings", *J. Med. Chem.* vol. 46, No. 24, pp. 5153-5161, (2003).
Bohl, et al., "Nitric oxide-generating polymers reduce platelet adhesion and smooth muscle cell proliferation", *Biomaterials*, vol. 21, pp. 2273-2278, (2000).
Braunhut, et al., "Modulation of Endothelial Cell Shape and Growth by Retinoids", *Microvas. Res.*, vol. 41, pp. 47-62, (1991).
Cagiannos, et al., "Rapamycin-coated expanded polytetrafluoroethylene bypass grafts exhibit decreased anastomotic neointimal hyperplasia in a porcine model", *J. of Vascular Surgery*, vol. 42, No. 5, pp. 980-988, (2005).
Choi, et al., "In vivo biocompatibility studies of poly (D, L-lactide)/poly(ethylene glycol)-poly(L-lactide) microspheres containing all-*trans*-retinoic acid", *J. Biomater. Sci. Polymer Edn.*, vol. 13, No. 3, pp. 301-322 (2002).
Choi, et al., "Inhibition of Tumor Growth by Biodegradable Microspheres Containing All-*trans*-Tretinoic Acid in a Human Head-And-Neck Cancer Xenograft", *Int. J. Cancer*: vol. 107, pp. 145-148, (2003).
Choi, et al., Long-term delivery of all-*trans*-retinoic acid using biodegradable PLLA/PEG-PLLA blended microspheres, *Int'l J. of Pharm.*, vol. 215, pp. 67-81, (2001).
DeRose, Jr., et al., "Retinoic acid suppresses intimal hyperplasia and prevents vessel remodeling following arterial injury", *Cardiovas. Surg.*, vol. 7, No. 6, pp. 633-639 (1999).
Frost, et al., "Synthesis, characterization, and controlled nitric oxide release from S-nitrosothiol-derivatized fumed silica polymer filler particles", *J. Biomed Mater Res.* 72A:, pp. 409-419, (2005).
Gaetano, et al., Retinoids Induce Fibroblast Growth Factor-2 Production in Endothelial Cells via Retinoic Acid Receptor α Activation and Stimulate Angiogenesis in Vitro and in Vivo, *Cir. Res.*, vol. 88, pp. e38-e47, (2001).
Giordano, et al., Sustained Delivery of Retinoic Acid from Microspheres of Biodegradable Polymer in PVR, *Invest. Ophthal. & Vis. Sci.*, vol. 34, No. 9, pp. 2743-2751, (1993).
Heise, et al., "PEG-hirudin/iloprost Coating of Small Diameter ePTFE Grafts Effectively Prevents Pseudointima and Intimal Hyperplasia Development", *Eur. J. Vasc. Endovas Surg.*, vol. 32, pp. 418-424 (2006).

Herdeg, et al., << Effects of local all-*trans*-retinoic acid delivery on experimental atherosclerosis in the rabbit carotid artery, *Cardiovas. Res.*, vol. 57, pp. 544-553, (2003).
Horie, et al., "Retinoic acid stimulates expression of thrombomodulin, a cell surface anticoagulant glycoprotein, on human endothelial cells", *Biochem. J.*, vol. 281, pp. 149-154, (1992).
Jeong, et al., Preparation of poly(DL-lactide-co-glycolide) microspheres encapsulating all-trans retinoic acid, *Int'l. J. of Pharm.*, vol. 259, pp. 79-91, (2003).
Johst, et al., All-Trans and 9-cis Retinoid Acids Inhibit Proliferation, Migration, and Synthesis of Extracellular Matrix of Human Vascular Smooth Muscle Cells by Inducing Differentiation In Vitro, *J. Cardiovasc. Pharm.*, vol. 41, No. 4, pp. 526-535, (2003).
Jun, et al., "Nitric Oxide-Producing Polyurethanes", *Biomacromolecules*, vol. 6, No. 2, pp. 838-844, (2005).
Kapadia, et al., "Modified Prosthetic Vascular Conduits", *Circulation*, vol. 117, pp. 1873-1882, (2008).
Lee, et al., "All-Trans-Retinoic Acid Attenuates Neointima Formation with Acceleration of Reendothelialization in Balloom-Injured Rat Aorta", *J. Korean Med. Sci.* vol. 15, pp. 31-36, (2000).
Lee, et al., "Paclitaxel-coated expanded polytetrafluoroethylene haemodialysis grafts inhibit neointimal hyperplasia in porcine model of graft stenosis", *Nephrol. Dial. Transplant.*, vol. 21, pp. 2432-2438, (2006).
Lim, et al., "A Novel Technique for Loading of Paclitaxel-PLGA Nanoparticles onton e PTFE Vascular Grafts", *Biotechnol. Prog.*, vol. 23, No. 3, pp. 693-697, (2007).
Leville, et al., "All-*trans*-retinoic acid decreases cell proliferation and increases apoptosis in an animal model of vein bypass grafting", *Surgery*, vol. 128, No. 2, pp. 178-184, (2000).
Leville, et al., "All-Trans-Retinoic Acid Decreases Vein Graft Intimal Hyperplasia and Matrix Metalloproteinase Activity in Vivo", *J. of Surg. Res.*, vol. 90, No. 2, pp. 183-190 (2000).
Medhora, et al., "Retinoic acid upregulates $\beta^1$-integrin in vascular smooth muscle cells and alters adhesion to fibronectin", *Am. J. Physiol. Heart Circ. Physiol.*, vol. 279, pp. H382-H387, (2000).
Miano, et al., "all-*Trans*-Retinoic Acid Reduces Neointimal Formation and Promotes Favorable Geometric Remodeling of the Rat Carotid Artery After Balloon Withdrawal Injury", *Circulation*, vol. 98, pp. 1219-1227, (1998).
Miano, et al., "Retinoid Receptor Expression and all-*trans* Retinoic Acid-Mediated Growth Inhibition in Vascular Smooth Muscle Cells", *Circulation*, vol. 93, pp. 1886-1895, (1996).
Ogle, et al., "Manipulation of Remodeling Pathways to Enhance the Mechanical Properties of a Tissue Engineered Blood Vessel", *J. of Biomech. Eng.*, vol. 124, pp. 724-733, (2002).
Orlandi, et al., Modulation of Clusterin Isoforms Is Associated With All-Trans Retinoic Acid-Induced Proliferative Arrest and Apoptosis of Intimal Smooth Muscle Cells, *Arterio. Throm. And Vasc. Bio.*, vol. 25, pp. 348-353, (2005).
Orlandi, et al., "Phenotypic Heterogeneity Influences Apoptotic Susceptibility to Retinoic Acid cis-Platinum of Rat Arterial Smooth Muscle Cells IN Vitro : implications for the Evolution of Experimental Intimal Thickening", *Arterioscler, Thromb. Vasc. Biol.*, vol. 21, pp. 1118-1123, (2001).
Pulfer, et al., "Incorporation of nitric oxide-releasing crosslinked polyethyleneimine microspheres into vascular grafts", *J. Biomed. Mater. Res*, vol. 37, pp. 182-189, (1997).
Reynolds, et al. "Nitric Oxide Releasing Polyurethanes with Covalently Linked Diazeniumdiolated Secondary Amines", *Biomacromolecules*, vol. 7, No. 3, pp. 987-994, (2006).
Smith, et al., "Nitric Oxide-Releasing Polymers Containing the [N(O)NO]⁻Group", *J. Med. Chem.*, vol. 39, No. 5, pp. 1148-1156, (1996).
Uruno, et al., "Upregulation of Nitric Oxide Production in Vascular Endothelial Cells by All-trans Retinoic Acid Through the Phosphoinositide 3-kinase/Akt Pathway", *Circulation*, vol. 112, pp. 727-736, (2005).

(56) References Cited

OTHER PUBLICATIONS

Walpoth, et al., "Prevention of neointimal proliferation by immunosuppression in synthetic vascular grafs", *Euro. J. of Cardiothor. Surg.*, vol. 19, pp. 487-492, (2001).

Wiegman, et al., "All-*trans*-Retinoic Acid Limits Restenosis After Balloon Angioplasty in the Focally Atherosclerotic Rabbitt : A Favorable Effect on Vessel Remodeling", *Arterioscler. Thromb. Vasc. Biol.*, vol. 20, pp. 89-95, (2000).

Yokota, et al., "Retinoic acid suppresses andothelin-1 gene expression at the transcription level in endothelial cells", *Atherosclerosis*, vol. 159, pp. 491-496, (2001).

Herdeg, et al., "Effects of Local All-Trans-Retinoic Acid Delivery on Experimental Atherosclerosis in the Rabbit Carotid Artery", *Cardiovascular Research*, 2003, vol. 57, pp. 544-553.

Lee, et al., "All-Trans-Retinoic Acid Attenuates Neointima Formation with Acceleration of Reendothelialization in Balloon-Injured Rat Aorta", *J. Korean Med. Sci.*, 2000, vol. 15, pp. 31-36.

Kooistra, T., et al., "Stimulation of Tissue-Type Plasminogen Activator Synthesis by Retinoids in Cultured Human Endothelial Cells and Rat Tissues in vivo," Thromb Haemost, May 6, 1991;65(5):565-72.

\* cited by examiner

CONTROLLED AND LOCALIZED RELEASE OF RETINOIDS TO IMPROVE NEOINTIMAL HYPERPLASIA

CROSS-REFERENCE TO RELATED APPLICATIONS

This application claims the benefit of the filing date of U.S. Provisional Application Ser. No. 61/077,949 filed 3 Jul. 2008, which is hereby incorporated by reference in its entirety.

FIELD OF THE INVENTION

The present disclosure relates to vascular implants incorporating all trans-retinoic acid or its derivatives reduce thrombosis and/or neointimal hyperplasia following surgical implantation.

BACKGROUND OF THE INVENTION

Atherosclerosis is prevalent in all developed nations and is the leading cause of death and disability in the United States. A debilitating and disabling sequela of atherosclerosis is peripheral arterial disease (PAD). Persons with PAD often have impaired function and quality of life, regardless of symptoms. For those with severe PAD, often lower extremity bypass grafting remains the only option for limb salvage.

The gold standard conduit for infrainguinal bypass grafting is autologous vein. While the patency for infrainguinal vein grafts remains approximately 70% at 5 years, vein is not available in approximately one-third of patients due to intrinsic venous disease or prior vein harvesting. In these cases, expanded polytetrafluoroethylene (ePTFE) grafts are the most commonly used alternative bypass conduit. However, the primary patency rates for infrapopliteal ePTFE bypass grafts are dismal. Prosthetic bypass graft failure occurs secondary to either progression of atherosclerotic disease, thrombosis, or development of neointimal hyperplasia.

Problems associated with using prosthetic grafts are so severe that cardiac surgeons do not use them for coronary artery bypass grafting (CABG). Patients that require CABG would benefit significantly from off-the-shelf prosthetic grafts as often times they do not have healthy veins or arteries to perform the procedure. Although ePTFE grafts are the current standard for prosthetic infrainguinal bypass grafting, they can be thrombogenic, especially when used in small diameter below-knee revascularization procedures. Stenosis due to neointimal hyperplasia remains a challenge to their long-term efficacy.

Several types of surface modification strategies have been utilized to change the nature of the interaction between blood and the prosthetic graft. Most of these strategies have focused on permanently immobilizing an antithrombogenic compound or creating a protein-resistant surface, with variable results. For example, heparin has been widely used as an antithrombotic and antiproliferative agent to modify the surface of vascular grafts in order to reduce thrombus formation and neointimal hyperplasia. In animal models, heparin-modified ePTFE grafts significantly reduced acute thrombosis and anastomotic neointimal hyperplasia. However, the possible formation of antiplatelet antibodies and the associated heparin-induced thrombocytopenia can result in deadly outcomes.

Therefore, there exists a need for improved graft modification technologies which enable treatment or inhibition of neointimal hyperplasia while avoiding systemic or toxic side effects.

SUMMARY OF THE INVENTION

Controlled release vascular implants, such as vascular grafts, stents, gels, and wraps, comprising a biocompatible polymer and all trans retinoic acid (ATRA), or its derivatives, can be used to treat, prevent, or inhibit thrombosis and neointimal hyperplasia which may otherwise be induced by prosthetic implantation. In particular, the implants described herein can inhibit smooth muscle cell proliferation, neointimal hyperplasia, and upregulate antithrombotic genes and nitric oxide production in the vasculature. Further, the implants are capable of delivering controlled and predictable localized concentrations of ATRA.

In one aspect, the present disclosure provides methods for reducing or preventing the occurrence of neointimal hyperplasia and/or thrombosis following implantation of a vascular implant, said method comprising, contacting a vascular implant with all-trans retinoic acid (ATRA); and implanting the vascular implant in a patient in need of thereof, wherein the vascular implant comprises a biocompatible polymeric matrix; and the vascular implant releases a therapeutically effective amount of ATRA sufficient to inhibit or prevent neointimal hyperplasia when implanted in the patient.

In a second aspect, the present disclosure provides methods for preparing a modified vascular implant, comprising, providing a vascular implant; and contacting the vascular implant with all-trans retinoic acid (ATRA) to yield a modified vascular implant, wherein the modified vascular implant comprises a biocompatible polymeric matrix; and the modified vascular implant releases a therapeutically effective amount of ATRA sufficient to inhibit neointimal hyperplasia and/or thrombosis when implanted in a patient.

DETAILED DESCRIPTION OF THE INVENTION

In a first aspect, the present disclosure provides methods for reducing or preventing the occurrence of neointimal hyperplasia following implantation of a vascular implant, said method comprising, contacting a vascular implant with all-trans retinoic acid (ATRA); and implanting the vascular implant in a patient in need of thereof.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician, which includes one or more of the following:

(1) preventing the disease; for example, preventing a disease, condition or disorder in an individual who may be predisposed to the disease, condition or disorder but does not yet experience or display the pathology or symptomatology of the disease;

(2) inhibiting the disease; for example, inhibiting a disease, condition or disorder in an individual who is experiencing or displaying the pathology or symptomatology of the disease, condition or disorder; and (3) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease.

The term "biocompatible", as used herein, is intended to describe materials that do not elicit a substantial detrimental response in vivo.

As used herein, "biodegradable" polymers are polymers that fully degrade under physiological or endosomal conditions. In preferred embodiments, the polymers and polymer biodegradation byproducts are biocompatible. Biodegradable polymers are not necessarily hydrolytically degradable and may require enzymatic action to fully degrade.

The phrase "endosomal conditions", as used herein, relates to the range of chemical (e.g., pH, ionic strength) and biochemical (e.g., enzyme concentrations) conditions likely to be encountered within endosomal vesicles. For most endosomal vesicles, the endosomal pH ranges from about 5.0 to 6.5.

The phrase "physiological conditions", as used herein, relates to the range of chemical (e.g., pH, ionic strength) and biochemical (e.g., enzyme concentrations) conditions likely to be encountered in the intracellular and extracellular fluids of tissues. For most tissues, the physiological pH ranges from about 7.0 to 7.4.

As used herein, the term "patient" refers to animals, including mammals, preferably humans.

In certain embodiments, the vascular implant as described above is a vascular graft, a vascular stent, a wrap, or a gel. In a particular embodiment, the vascular implant is a vascular graft. In another particular embodiment, the vascular implant is a vascular stent. In another particular embodiment, the vascular implant is a wrap, such as an anastomoses wrap. In another particular embodiment, the vascular implant is a gel. Such wraps and gels may be placed around at least a portion of a vascular graft or stent for implantation. Thereby, a vascular implant can comprises a wrap or gel comprising the biocompatible polymeric matrix and ATRA and a vascular stent or graft, wherein the wrap or gel is placed around at least a portion of the vascular stent or graft.

In another embodiment, a vascular graft can be implanted in a patient in need thereof according to methods known to one skilled in the art, and then a wrap or gel comprising the biocompatible polymeric matrix and ATRA can be placed around at least a portion of the implanted vascular graft and at least a portion of the blood vessel into which the graft has been implanted. As such, ATRA can diffuse through the vascular graft and the blood vessel into which the graft has been implanted in order to prevent and/or inhibit neointimal hyperplasia.

In another embodiment, a vascular graft which has been coated over at least a portion of its exterior surface with a wrap or gel comprising the biocompatible polymeric matrix and ATRA can be implanted in a patient in need thereof according to methods known to one skilled in the art.

In another embodiment, a vascular stent can be implanted in a patient in need thereof according to methods known to one skilled in the art, and then a wrap or gel comprising the biocompatible polymeric matrix and ATRA can be placed onto at least a portion of the interior surface of the implanted stent.

In another embodiment, a vascular stent which has been coated over at least a portion of its exterior surface with a wrap or gel comprising the biocompatible polymeric matrix and ATRA can be implanted in a patient in need thereof according to methods known to one skilled in the art. As such, the wrap or gel can be entrapped between the exterior surface of the vascular stent and the interior surface of the blood vessel into which the stent has been implanted.

The vascular implants generally comprise a biocompatible polymeric matrix. For example, the biocompatible polymeric matrix can comprise a polyester, polyurethane, polycarbonate, polyanhydride, polyphosphoester, or a mixture thereof. The biocompatible polymeric matrix can be elastomeric; or the biocompatible polymeric matrix can be a gel.

As used herein, an elastomer is a macromolecular material that can return rapidly to the approximate shape from which it has been substantially distorted by a weak stress. For example, rubber is a common elastomer.

The term "gel" as used herein is directed to a continuous three-dimensional crosslinked polymeric network integrating a liquid into the interstices of the network. The crosslinked polymeric network provides the gel structure. Depending upon their degree of structure, gels can have a broad spectrum of properties, ranging from flowing gels which are slightly more viscous than water to nonflowing gels which are very rigid. The term "flowing gels" as used herein refers to gels which flow under the force of gravity when unconfined at ambient atmospheric conditions. "Nonflowing gels" do not flow under these conditions.

In certain embodiments, the biocompatible polymeric matrix is a polyester, such as a poly(citric acid-diol) or a poly(glycerol-diacid).

A poly(citric acid-diol), as used herein, is a polyester prepared from citric acid (a tri-carboxylic acid monomer), and a second monomer comprising two alcohol functional groups (a "diol") according to methods familiar to one skilled in the art. For example, suitable poly(citric acid diols) can be prepared as described in U.S. Patent Application Publication Nos. 2005/0063939 and 2007/0208420, which are hereby incorporated by reference in their entirety. Examples of diols include, but are not limited to, aromatic-diols (e.g., hydroquinone, catechol, resorcinol), $C_2$-$C_{20}$ alkyl-diols, $C_2$-$C_{20}$ alkenyl-diols (e.g., tetradeca-2,12-diene-1,14-diol), and mixtures thereof. The diols may also include substituents as well. Reactive groups like amines and carboxylic acids will increase the number of sites available for cross-linking. Amino acids and other biomolecules will modify the biological properties of the polymer. Aromatic groups, aliphatic groups, and halogen atoms will modify the inter-chain interactions within the polymer. Diols further include macromonomer diols such as polyethylene oxides, and N-methyldiethanolamine (MDEA).

In certain embodiments, the diol comprises one or more $C_2$-$C_{20}$ alkyl-diols, $C_2$-$C_{20}$ alkenyl-diols, or mixtures thereof. In certain other embodiments, the diol comprises one or more $C_2$-$C_{20}$ alkyl-diols, such as a $C_6$-$C_{20}$ alkyl-diol, or a $C_6$-$C_{14}$ alkyl-diol, or a $C_6$-$C_{12}$ alkyl-diol. For example, the diol can comprise an $\alpha,\omega$-$C_2$-$C_{20}$ alkanediol, such as 1,12-dodecanediol, 1,10-decanediol, 1,8-octanediol, or a mixture thereof. In another example, the diol can comprise 1,10-decanediol, 1,8-octanediol, or a mixture thereof. In another example, the diol can comprise 1,8-octanediol (e.g., the polyester is poly(1,8-octanediol-citrate).

The poly(citric acid-diol) may be crosslinked, for example, by optionally including one or more hyperbranching monomers, such as a monomer comprising three alcohol functional groups (a "triol"), in order to control the degradation thereof. For example, glycerol can be added in addition to the citric acid and diol monomer (0-3 mol %, provided the molar ratio of carboxyl and hydroxyl group among the three monomers was maintained as 1/1). Glycerol is a hydrophilic component, and its addition can facilitate the water penetration into the network films which results in the faster degradation rate. Increasing amounts of glycerol can increase the break strength and Young's modulus of the resulting polyester. For example, the Young's modulus can range from 1 to 16 MPa, with strengths and strains at break of up to 10 MPa and 500%, respectively. Depending on the synthesis conditions, total degradation time may range from months to years. Degradation within 6 to 12 months is preferred.

A poly(glycerol-diacid), as used herein, is a polyester which is prepared from a triol monomer, glycerol, and a second monomer comprising two carboxylic acid functional groups (a "diacid") according to methods familiar to one skilled in the art. For example, suitable poly(glycerol-diacid)s can be prepared as described in U.S. Patent Application Publication No. 2003/0118692, which is hereby incorporated by reference in its entirety. Examples of diacids include, but are not limited to, aromatic-diacids (e.g., terephthalic acid and carboxyphenoxypropane), $C_2$-$C_{20}$ alkyl-diacids, $C_2$-$C_{20}$ alkenyl-diacids, and mixtures thereof. The diacids may also include substituents as well. Reactive groups like amine and hydroxyl will increase the number of sites available for cross-linking. Amino acids and other biomolecules will modify the biological properties of the polymer. Aromatic groups, aliphatic groups, and halogen atoms will modify the inter-chain interactions within the polymer.

In certain embodiments, the diacid comprises one or more $C_2$-$C_{20}$ alkyl-diacids, $C_2$-$C_{20}$ alkenyl-diacids, or mixtures thereof. In certain other embodiments, the diacids comprises one or more $C_2$-$C_{20}$ alkyl-diacids. For example, the diacid can comprise an $\alpha,\omega$-$C_2$-$C_{20}$ alkanediacid, such as, sebacic acid, malonic acid, succinic acid, glutaric acid, adipic acid, pimelic acid, suberic acid, azelaic acid, or a mixture thereof. In another example, the diacid can comprise sebacic acid (e.g., the polyester is poly(glycerol-sebacate).

The poly(glycerol-diacid) may be crosslinked, for example, by including one or more hyperbranching monomers, such as a monomer comprising three carboxylic acid functional groups (a "triacid"), may be optionally included in the poly(glycerol-diacid), in order to control the degradation thereof. For example, citric acid can added in addition to the glycerol and diacid monomers (0-3 mol %, provided the molar ratio of carboxyl and hydroxyl group among the three monomers was maintained as 1/1).

The elastic modulus and degradation rate of the polymer is easily adjusted by modifying the cross-link density. In certain embodiments, the cross-link density of elastomeric polymers produced according to the invention may be 40% or less, less than 30%, less than 20%, less than 10%, or less than 5%. The polymer may have a crosslink density of 40% or less, less than 30%, less than 20%, less than 20%, less than 5%, less than 1%, less than 0.5%, or less than 0.05%.

In one embodiment, the glycerol-diacid copolymers of the invention have a tensile elastic modulus of 5 MPa or less. One skilled in the art will recognize that the modulus of the polymer may be adjusted depending on the application. For example, the polymer may have a modulus less than 3 MPa, less than 1 MPa, less than 0.5 MPa, less than 0.3 MPa, or less than 0.1 MPa. The polymer may have a maximum elongation greater than 250%.

Catalysts may be used to reduce reaction temperature, shorten reaction time, and increase individual chain length for preparation of the polyesters described above. However, the catalyst should be biocompatible or easily removed. An exemplary FDA-approved catalyst is stannous octoate (bis(2-ethylhexanoate)tin(II)).

ATRA can be incorporated into the biocompatible polymeric matrix, for example, as microparticles or nanoparticles comprising the ATRA which can be embedded within the biocompatible polymeric matrix. In another embodiment, ATRA can be incorporated in the biocompatible polymeric matrix as microparticles and/or nanoparticles of ATRA.

Alternatively, the ATRA can be incorporated into the biocompatible polymeric matrix by encapsulation in micelles or liposomes, wherein the micelles or liposomes are embedded within the biocompatible polymeric matrix. In another alternative, the ATRA can be absorbed, suspended, or dissolved within the biocompatible polymeric matrix. In certain embodiments, the ATRA is suspended or dissolved within the biocompatible polymeric matrix. In certain other embodiments, the ATRA is absorbed by the biocompatible polymeric matrix.

The vascular implants as described according to any of the preceding embodiments, can release a therapeutically effective amount of ATRA sufficient to inhibit or prevent neointimal hyperplasia and/or thrombosis when implanted in a patient.

In one embodiment, the ATRA can be released from the vascular implants at a rate of about 0.001 to 5 mg per gram of polymer per day when measured according to high performance liquid chromatography (in vitro). In certain embodiments, the ATRA is released from the vascular implants at a rate of about 0.001 to 1.2 mg per gram of polymer per day; or about 0.001 to 0.78 mg per gram of polymer per day; or about 0.001 to 0.58 mg per gram of polymer per day. In a particular embodiment, the ATRA is released from the vascular implants at a rate of about 0.001 to 0.39 mg per gram of polymer per day.

In another embodiment, the vascular implant, as defined by any one of the preceding embodiments, can comprise about 0.001 to 15 wt % ATRA with respect to the biocompatible polymeric matrix. In certain embodiments, the vascular implant comprises about 0.001 to 10 wt %; or about 0.001 to 7.5 wt %; or about 0.001 to 5 wt % ATRA with respect to the biocompatible polymeric matrix. In a particular embodiment, the vascular implant comprises about 0.001 to 3 wt % ATRA with respect to the biocompatible polymeric matrix.

In yet another embodiment, the therapeutically effective amount of ATRA can be released by the vascular implant, as defined by any one of the preceding embodiments, for a period of about 1 day to about 12 weeks. In particular, the therapeutically effective amount of ATRA can be released by the vascular implant, as defined by any one of the preceding embodiments, for a period of about 1 day to 10 weeks; or about 1 day to 8 weeks; or about 1 day to 6 weeks. In certain embodiments, the therapeutically effective amount of ATRA can be released by the vascular implant, as defined by any one of the preceding embodiments, for a period of about 1 day to 4 weeks.

Further, the biocompatible polymeric matrix coating comprising the ATRA in any of the preceding embodiments can have a thickness ranging from about 0.01 to 3 mm; or about 0.1 to 3 mm. In certain embodiments, the biocompatible polymeric matrix coating comprising the ATRA in any of the preceding embodiments can have a thickness ranging from about 1 to 10 μm or 2 to 5 μm.

In one embodiment of the first aspect, the present disclosure provides methods for reducing or preventing the occurrence of neointimal hyperplasia following implantation of a vascular implant as described according to any of the preceding embodiments.

ATRA

All-trans retinoic acid (ATRA) is a hydrophobic, lipid- and ethanol-soluble compound which, in vitro, has demonstrated a multitude of vasoprotective properties, including inhibition of vascular smooth muscle cell (VSMC) migration, VSMC proliferation, and extracellular matrix production (see, for example, Miano et al. Circulation 1996 May 15; 93(10): 1886-95; and Johst U, et al. J Cardiovasc Pharmacol 2003 April; 41(4):526-35.) ATRA stimulates VSMC apoptosis (see, for example, Orlandi, A. et al. Arterioscler Thromb Vasc Biol 2005 February; 25(2):348-53; and Orlandi, A. et al., Arterioscler Thromb Vasc Biol 2001 July; 21(7):1118-23). With respect to endothelial cells, ATRA has been shown to modulate endothelial cell growth and phenotype (see, for example, Braunhut, S. J. et al., Microvasc Res 1991 January;

41(1):47-62; and Gaetano, C. et al., Circ Res 2001 Mar. 2; 88(4):E38-E47). Further, ATRA has been shown to increase nitric oxide synthesis and thrombomodulin release from endothelial cells (see, for example, Achan, V. et al., Circ Res 2002 Apr. 19; 90(7):764-9; and Horie, S. et al., Biochem J 1992 Jan. 1; 281 (Pt 1):149-54). Other vasoprotective effects of ATRA include inhibition of endothelin-1, stimulation of plasminogen activator synthesis, and increased beta 1 integrin expression (see, for example, Yokota, J. et al. Atherosclerosis 2001 December; 159(2):491-6; Kooistra, T. et al., Thromb Haemost 1991 May 6; 65(5):565-72; and Medhora, M. M., Am J Physiol Heart Circ Physiol 2000 July; 279(1): H382-H387). When provided systemically or locally, in vivo, to balloon-injured rodents and rabbits, ATRA has been shown to affect the vasculature, including, inhibition of neointimal hyperplasia, inhibition of vascular remodeling, accelerated reendothelialization, and prevention of restenosis in atherosclerotic rabbits. (See, for example, Miano, J. M. et al., Circulation 1998 Sep. 22; 98(12):1219-27; DeRose, Jr., J. J. et al. Cardiovasc Surg 1999 October; 7(6):633-9; Lee, C. W. et al., J Korean Med Sci 2000 February; 15(1):31-6; Wiegman, P. J. et al., Arterioscler Thromb Vasc Biol 2000 January; 20(1):89-95; Herdeg, C. et al., Cardiovasc Res 2003 February; 57(2): 544-53; Leville, C. D. et al., J Surg Res 2000 May 15; 90(2): 183-90; and Leville, C. D. et al., Surgery 2000 August; 128 (2):178-84.) Although encouraging, in vivo delivery of ATRA has not been localized or sustained in these studies. More important, no studies have been done with ATRA in the context of inhibiting neointimal hyperplasia in prosthetic grafts.

Implant Preparation

The preceding vascular implants can be prepared according to a method comprising, providing a vascular implant; and contacting the vascular implant with all-trans retinoic acid (ATRA) to yield a modified vascular implant. Generally, the modified vascular implant comprises a biocompatible polymeric matrix as described above and releases a therapeutically effective amount of ATRA sufficient to inhibit neointimal hyperplasia when implanted in a patient.

In certain embodiments, the vascular implant is a vascular graft, a vascular stent, a wrap, or a gel. In a particular embodiment, the vascular implant is a vascular graft. In another particular embodiment, the vascular implant is a vascular stent. In another particular embodiment, the vascular implant is a wrap. In another particular embodiment, the vascular implant is a gel.

The vascular implant itself can be formed from biocompatible materials known to one skilled in the art. For example, vascular grafts can be formed from poly(ethylene terephthalate) (PETE, Dacron™) or poly(tetrafluoroethylene), such as expanded poly(tetrafluoroethylene) (ePTFE). Vascular stents can be formed from stainless steel or a cobalt-chromium alloy or nitinol.

In one embodiment, the contacting of the vascular implant with all-trans retinoic acid (ATRA) can comprise coating the vascular implant with a mixture comprising a biocompatible polymer prepolymer and nanoparticles, microparticles, micelles, or liposomes comprising ATRA. ATRA can readily be incorporated into micro- and nanoparticles, micelles, and/or liposomes using a standard techniques known to those skilled in the art. The nanoparticles, microparticles, micelles, and/or liposomes can then be embedded within the biocompatible matrix of a coated vascular implant as noted above. In certain embodiment, the coated implant can be set, for example, by heating under vacuum to form a coherent film on the surface of the implant comprising the biocompatible polymer and nanoparticles, microparticles, micelles, or liposomes comprising ATRA. When heating the implant, the temperature should be maintained at a suitable temperature which does not cause degradation of the ATRA embedded therein. For example, the implants can be heated at a temperature of about 40 to 60° C. for about 4 days.

The term "prepolymer" as used herein refers to a material which can be processed to form a coherent polymer film or matrix generally having either a higher molecular weight or higher crosslink density than the prepolymer. A prepolymer, for example, can be coated onto an object either as a liquid, oil, syrup, or from a solution and further processed to form a coherent polymer film or matrix by, for example, heating or contacting the coated object with a polymerization catalyst. Examples of prepolymers include, but are not limited to, polyester prepolymers. For example, a polyester prepolymer can be coated onto an object and set by heating to form a coherent polyester film or matrix having a higher molecular weight or higher crosslink density than the prepolymer.

In another embodiment, the contacting of the vascular implant with all-trans retinoic acid (ATRA) can comprise soaking the vascular implant in a solution comprising ATRA. Although ATRA is not readily soluble in water, it is partly soluble in ethanol (3 mg/ml), and soluble in dimethylsulfoxide (DMSO). It is also soluble in chloroform and dichloromethane, solvents commonly used to process biodegradable polyester thermoplastics that are used in biomedical applications.

In another embodiment, the contacting of the vascular implant with all-trans retinoic acid (ATRA) can comprise coating the vascular implant with a biocompatible polymer prepolymer; setting the coated vascular implant; and soaking the coated vascular implant in a solution comprising ATRA. Setting the coated vascular implant can include heating the vascular implant, optionally under a static or dynamic vacuum, to encourage the film to cross-link or otherwise convert to a coherent film which substantially coats the desired portion of a vascular implant. In certain embodiments, when the coated vascular implant is soaked in a solution comprising ATRA, the solution causes the biocompatible polymeric matrix to swell.

In another embodiment, the contacting of the vascular implant with all-trans retinoic acid (ATRA) can comprise coating the vascular implant with a mixture comprising ATRA and the biocompatible polymeric matrix, wherein the biocompatible polymeric matrix is a biocompatible thermoplastic polymer.

In another embodiment, a wrap or gel comprising ATRA and the biocompatible polymer can be placed around at least a portion of a standard vascular graft or stent for implantation in a patient in need thereof as described above. Such wraps and gels can be prepared as described above. For example, a prepolymer, as described above, can be polymerized to provide a wrap or gel which can be contacted with a solution comprising ATRA to provide an ATRA containing wrap or gel. Alternatively, a prepolymer comprising ATRA can be can be polymerized to provide to provide an ATRA containing wrap or gel. The wrap or gel can be contacted with a solution comprising ATRA prior to being placed around at least a portion of a vascular graft or stent; or alternatively, the wrap or gel can be placed around at least a portion of a vascular graft or stent, and then the coated graft or stent can be contacted with a solution comprising ATRA.

EXAMPLES

Example 1

Poly(1,8 octanediol-co-citrate)(POC) Pre-polymer Synthesis

Equimolar amounts of citric acid and 1,8-octanediol are melted together at 160° C. while stirring for 15 minutes The temperature can be subsequently decreased to 140° C. and the mixture stirred for 1 hour. The pre-polymer can then be purified by dissolution in ethanol followed by precipitation in water and freeze-dried. For surface modification of an ePTFE graft, POC pre-polymer is dissolved in ethanol or 1,3-dioxolane to a concentration of 10% (w/v). See, for example, Yang J, Webb A R, Pickerill S J, Hageman G, Ameer G A. Synthesis and evaluation of poly(diol citrate) biodegradable elastomers. Biomaterials 2006 March; 27(9):1889-98; and Yang J, Webb A R, Ameer G A. Novel citric acid-based biodegradable elastomers for tissue engineering. Adv Mater 2004; 16(6):511-6, each of which are hereby incorporated by reference in their entirety).

The mechanical properties of the preceding elastomer can be modulated by controlling synthesis conditions such as crosslinking temperature and time, vacuum, choice of diol, and initial monomer molar ratio. Young's modulus can range from 1 to 16 MPa, with strengths and strains at break of up to 10 MPa and 500%, respectively. Depending on the synthesis conditions, total degradation time may range from months to years.

Increasing the molar ratio of citric acid increases the degradation rate of the copolymer without sacrificing its initial tensile strength. Likewise, degradation can be modulated by including glycerol (2.5 mole %). Degradation of this glycerol-containing elastomer in phosphate buffered saline (PBS) at 37° C. was enhanced almost 2-fold after 4 months of incubation.

Example 2

In Vitro Evaluation of Clotting and Inflammatory Characteristics of POC

Re-calcification clotting assays were performed to assess the clotting kinetics of POC relative to tissue culture polystyrene and PLGA. Briefly, test and control polymer samples in 96-well plates were incubated in acid citrate dextrose (ACD) anticoagulated human or pig platelet poor plasma (PPP). Immediately prior to absorbance measurement, $CaCl_2$ (0.025 M) was added to each well to initiate clotting. The absorbance of each well was monitored every 30 seconds for 30 minutes at 405 nm. The rate of clot formation is consistently lower for plasma exposed to POC when compared to the other materials (slope of linear region=0.088±0.027, 0.089±0.013, and 0.025±0.019 A.U./min, for TCP, PLGA, and POC, respectively). This finding may be explained by the presence of the hydroxyl, carboxyl, and potentially chelating citric acid functional groups within the POC.

For assessment of inflammatory potential, a suspension of human monocytic THP-1 cells was exposed to POC, TCP, PLGA, and ePTFE films. Afterwards, the expression of tissue factor, IL-6, and TNF-α was measured via ELISA. Addition of lipopolysaccharide (LPS) to the cells was used as a positive control. Results are shown in Table 1.

TABLE 1

|  | TCP | ePTFE | PLGA | POC | LPS |
|---|---|---|---|---|---|
| Tissue factor | 208 ± 26 | 96 ± 27 | 114 ± 12 | 9 ± 2* | 536 ± 81 |
| TNF-α | 12 ± 2 | 21 ± 3 | 15 ± 5 | 17 ± 5 | 874 ± 531 |
| IL-6 | 1.4 ± 0.05 | 32 ± 5 | 8 ± 4 | 2.8 ± 2* | — |

POC did not elicit a significant upregulation of these markers relative to the other materials. In fact, POC was less reactive than ePTFE regarding tissue factor and IL-6 expression.

Example 3

Modification of ePTFE Grafts with POC

Prior to modification, standard-wall non-stretch ePTFE grafts were cleaned by first soaking under sonication in absolute ethanol, acetone, and vacuum drying. The lumen of ePTFE grafts were modified by mechanically coating a layer of POC through a spin-shearing method. Briefly, a 5 mm diameter glass rod was dipped into 10% POC pre-polymer (pre-POC, Example 1) solution in 1,4-dioxane and inserted horizontally into the motor of a mechanical stirrer. The pre-POC-coated glass rod was spun clockwise at 300 rpm for 2 minutes and a 6 cm-long piece of ePTFE graft was placed concentrically over the spinning rod. The lumen of the graft was sheared against the spinning rod for 2 minutes by manually rotating the graft counterclockwise. The above procedure was considered to be 1 coating. To change the amount of POC deposited onto the graft (and, therefore, the coating thickness), the above procedure was repeated 3 and 6 times (defined as 3 and 6 coatings) to assess POC coverage and effects on graft compliance with increasing polymer content. After air-drying, the pre-POC-coated ePTFE graft was put into an oven at 80° C. for 2 days to obtain POC-ePTFE grafts.

For characterization, samples were cut into 1 $cm^2$ pieces. Changes in surface characteristics of the POC-modified ePTFE samples were assessed via SEM, water-in-air contact angle measurement, Fourier transform infrared (FTIR) analysis, and x-ray photoelectron spectroscopy (XPS) analysis. The compliance of the modified grafts was also measured. Sampling from several sections of the grafts confirmed uniform coatings of the PTFE fibrils and nodes. The thickness of the POC coating is approximately 2-5 microns. Equilibrium water-in-air contact angles of POC-ePTFE versus unmodified ePTFE were 36° and 120°, respectively. FTIR and XPS confirmed the presence of carboxyl and hydroxyl groups within the lumen of the graft. Three coatings or treatments with POC did not have an effect on the compliance of the native graft. The small decrease in compliance with 6 coatings may be explained by a severe disruption of the graft's fibril-node microarchitecture.

Example 4

Surface Modification of ePTFE Graft with POC and Drug Loading

Prior to modification, standard-wall non-stretch ePTFE grafts are cleaned by first soaking under sonication in absolute ethanol and vacuum drying. A POC infusion method is used in order to ensure a large amount of POC available for drug loading. POC is infused through the vessel wall by clamping one end of the graft and pumping the POC pre-polymer solution (Example 1) into the graft and through the vessel wall. After infusing polymer through the graft wall and drying, the lumen of ePTFE grafts is modified by mechanically coating a layer of POC through a spin-shearing method.

A 5 mm diameter glass rod is dipped into 10% POC pre-polymer solution in 1,3-dioxolane and inserted horizontally into the motor of a mechanical stirrer. The pre-POC-coated glass rod is spun clockwise at 300 rpm for 2 minutes and an 8 cm-long piece of ePTFE graft placed concentrically over the spinning rod. The lumen of the graft is sheared against the spinning rod for 2 minutes by manually rotating the graft counterclockwise. The above procedure is considered to be 1 coating. A total of 3 coatings can be applied to the graft as it has been shown that up to 3 coatings can be applied without significantly affecting compliance. The coating is uniform and can remain intact after one month of implantation in vivo. After air-drying, the pre-POC-coated ePTFE graft is placed into an oven for post-polymerization.

Dosing of retinoic acid (ATRA) is controlled through the drug release rate which can be controlled by changing the POC polymerization conditions to vary the degree of swelling in aqueous media. For a faster release rate, coated grafts are polymerized at 80° C. for 2 days. Slower releasing grafts are polymerized for an additional 2 days at 80° C. Alternatively, 1,12 dodecanediol can be added to confer hydrophobicity to the coating. ATRA is loaded and sterilized at the same time by soaking the coated graft in a retinoic acid solution in ethanol (3 mg/ml) at room temperature in the dark for 24 hours. After removal from the ATRA solution, the grafts are freeze dried in sterile containers to collapse the polymer and entrap the ATRA. The amount of ATRA loaded in the polymer film can be indirectly determined by measuring the concentration of ATRA remaining in the ethanol solution after soaking. The concentration of ATRA in solution can be determined spectrophotometrically at 350 nm and compared to a standard curve.

Example 5

ATRA Release Kinetics and POC Stability

To measure the release, isomerization, and degradation of retinoic acid from POC, disks (10 mm diameter, 1 mm thick) and small segments of ATRA-loaded POC-ePTFE graft (1 cm length, 6 mm diameter) can be placed in culture medium and the drug release and POC degradation monitored over a period of 6 months. POC degradation can be assessed via mass loss and SEM. The supernatant can be removed from the disk or graft segment and replaced with fresh medium. Briefly, 350 µL can be taken from the medium at various time points and 50 µL of 1 M sodium acetate and 600 µL of acetonitrile can be added. After vortexing and centrifuging, 720 µL of the supernatant can be placed in a 2 mL glass autosampler vial along with 240 µL of water. After inversion mixing, the vial can be placed in the autosampler at 4° C. and the drug content determined using reverse-phase HPLC with UV-Vis detector at 340 nm.

Retinoids can be identified using external standards for 4-oxo-trans-retinoic acid, 4-oxo-cis-retinoic acid, 13-cis-retinoic acid, and ATRA. Supernatants can also be assessed for ATRA activity. Non-drug loaded POC-ePTFE grafts and uncoated ePTFE grafts can be used as controls. Also, ATRA-loaded POC-ePTFE grafts (9 cm length, 6 mm diameter) can be placed in a pulsatile flow circuit (1 Hz) to mimic dynamic conditions found in vivo. Cell culture medium can be perfused, single pass at 200 and 300 mL/min (flow rates typical of carotid and medium size arteries) and samples can be collected downstream from the graft. Samples can be assessed for ATRA concentration and activity (and POC fragmentation). These experiments can provide some insight into ATRA concentrations in the bulk flow at the distal anastomosis and effects on endothelial and smooth muscle cells.

Example 6

Cellular Responses of Released ATRA

The activity of the released ATRA can be assessed using both porcine and human aortic smooth muscle and endothelial cells as previously described. Human aortic smooth muscle (HASMC) and endothelial cells (HAEC) can be purchased from Lonza (Lonza, Allendale, N. J.). Porcine aortic smooth muscle (PASMC) and endothelial cells (PAEC) can be purchased from Cell Applications Inc. (Cell Applications, Inc., San Diego, Calif.). Samples collected from the static and flow drug release studies can be directly added to the wells to assess the effect of released ATRA on cells (i.e. ATRA activity). Positive controls can consist of adding ATRA-dissolved in DMSO or ethanol to the cells. These experiments can be also conducted with ATRA-loaded POC-ePTFE segments placed directly in the wells (1 cm length, 6 mm diameter).

Cell Proliferation:

HASMC, PASMC, HAEC, and PAEC can be seeded on 6-well plates at a density of 5000 cells/cm$^2$. The next day, the baseline number of intact cells can be determined using a Picogreen DNA assay kit (Invitrogen, Carlsbad, Calif.) after trypsinizing and pelleting the cells. The graft segment can then be placed above the cells in a transwell insert and at various time points the number of cells can be determined using a Picogreen DNA assay.

Cell Migration:

The migration of smooth muscle cells can be examined alone and in the presence of endothelial cells. To test the migration without endothelial cells, smooth muscle cells can be seeded at a density of 5000 cells/cm$^2$ in 6-well plates. After the cells reach confluence, the culture can be scraped with a silicon-coated stick to obtain a 0.8 mm wide in vitro wound and photographed using a Nikon microscope (Nikon Eclipse, TE2000-U) equipped with a photometrics CoolSNAP HQ (Silver Spring, Md.). A graft segment can then be placed in each well. After 24 hours, the graft can be removed and cells can be stained with propidium iodide to count migrating cells invading the empty space. At least 6 images from the empty space can be used and results counted as the total number of migrating cells per field. To examine smooth muscle cell migration in the presence of endothelial cells, a transfilter system can be prepared as previously described. Briefly, Nucleopore polycarbonate filters (5 µm pore size) can be inserted between an inner and outer polycarbonate frame. In this way, two separate compartments are created in which endothelial cells and smooth muscle cells can be seeded. The 5 µm pore size can allow the migration of smooth muscle cells from the upper to the lower chamber as shown previously. Endothelial cells can be seeded at a density of 5000 cells/cm$^2$ on the lower filter side. After 24 hours, smooth muscle cells can be seeded on the upper filter side and a graft segment added to the lower compartment. After 14 days in culture, the total number of cells on both sides of the filter can be determined using a Picogreen DNA assay after disaggregation with trypsin/EDTA. Cell proliferation and migration can be compared among all experimental groups. As shown in previous experiments, endothelial cells should stop proliferating once confluence is reached, therefore any increase in the number of cells should be due to smooth muscle cell proliferation and migration.

Nitric Oxide Release:

Endothelial cells can be examined for nitric oxide release in response to ATRA. Intracellular nitric oxide can be examined using a nitric oxide synthase detection kit according to manufacturer's instructions (Cell Technology Inc, Mountain View, Calif.). Nitric oxide production can be determined by measuring fluorescence intensity with excitation at 495 nm and emission at 510 nm. Extracellular nitric oxide production can be assessed using a nitric oxide analyzer (Apollo 4000, World Precision Instruments, Sarasota, Fla.).

Protein Expression and Synthesis:

Protein expression and synthesis can be measured concurrently with cell proliferation. Smooth muscle cells can be probed for smooth muscle α-actin and heavy chain myosin via immunohistochemistry and western blotting to assess differentiation. The ability of the cells to remodel the extracellular matrix can be assessed by staining for matrix metalloproteinase-2 and matrix metalloproteinase-9. Detection can then be performed using horseradish peroxidase-linked secondary antibodies and chemiluminescence detection via a UVP Biochemi gel documentation system (UVP, Inc, Upland, Calif.). Collagen and elastin synthesis can be determined using the Sircol collagen and Fastin elastin assay kits (Accurate Chemical Co., Westbury, N.Y.).

Example 7

Surgical Implantation and In Vivo Graft Assessment

Grafts can be sterilized during the loading step by soaking in retinoic acid in ethanol and placed in sterile containers for freeze drying. Conventional pigs can be fasted overnight prior to the day of surgery but allowed ad libitum access to tap water. The animals can receive pre-op analgesia with buprenorphine (0.01 mg/kg IM), and sedation with Acepromazine (0.15 mg/kg IM) and Ketamine (20 mg/kg IM). After intubation, maintenance anesthesia can be conducted with Isoflurane (0.5-2.0%) delivered with 100% oxygen.

Procedure #1 (Carotid Artery Bypass Graft):

Male pigs (30-35 kg) can undergo vascular graft implantation in the carotid arteries. Bilateral common carotid arteries (CCAs) can be exposed through a midline neck incision. Five minutes before CCA occlusion, heparin (150 U/kg) can be administered intravenously. A 6 cm long segment of the graft (6 mm thin-walled non-stretch non-ringed ePTFE, POC-coated and either drug loaded or untreated) can be anastomosed to the proximal and distal CCA in a standard end-to-side configuration using 6-0 polypropylene stures. The carotid artery can be ligated to simulate an arterial occlusion. Prior to completion of the anastomosis, the vessel can be back-bled and flushed with heparinized saline. After completion of the anastomoses, flow can be restored and manually confirmed with palpation. The neck incisions can be closed with absorbable suture. Heparin can not be administered after surgery. Postoperative analgesia can be provided with buprenex (0.005-0.01 mg/kg IM) every 12 hours×48 hours. This procedure can be conducted on the left and right CCA, as two grafts can be implanted per animal. Aspirin (325 mg daily) can be given as an antiplatelet therapy pre- and post-operatively.

Procedure #2

(2D contrast angiography): Angiograms can be performed via a 6F sheath inserted into the right common femoral artery percutaneously and advanced into the proximal CCA under fluoroscopic guidance. Selective angiograms of both carotid artery bypass grafts can be obtained using 10 cc of a non-iodinated contrast agent (visipaque or omnipaque). Following completion of the angiogram, the guidewire and catheter can be removed.

Procedure #3 (MRA):

In lieu of contrast angiography, grafts may be assessed for patency and flow using Magnetic Resonance Imaging Analysis (MRA). The animals can undergo general anesthesia as described above, and receive a gadolinium-based contrast agent intravenously in order to obtain MRA images.

Procedure #4 (Ultrasonography):

Grafts also can be evaluated by duplex ultrasonography prior to harvesting to assess patency and obtain velocity measurements [peak systolic (PSV) and end diastolic velocity (EDV)] throughout the graft to evaluate for areas of stenoses. A significant stenosis can be defined as a PSV greater than two times the normal inflow artery velocity. Following harvest of the grafts, the animal can undergo euthanasia via pentobarbital overdose and bilateral thoracotomy.

Example 8

Graft Processing and Analysis

The grafts and adjacent 3 cm segments of the native vessel at each anastomosis can be harvested and cut into two parts from the middle (distal and proximal specimens). In select animals, a section of the graft can be opened longitudinally, photographed, and assessed for percent thrombus-free surface area. A 0.5 cm-long section of the graft from the distal and proximal specimens can be fixed in a 2.5% glutaraldehyde solution for morphological assessment via SEM The rest of the specimen can be fixed in 10% neutral buffered formalin, embedded in paraffin, and cut into 5 micron sections.

All grafts can be assessed for: a) neointimal hyperplasia (H&E), b) cellular proliferation (H&E stain, anti-Ki67) and differentiation (α actin and heavy chain myosin); b) collagen and elastin (Masson's trichrome and modified elastin van Gieson stain, respectively); c) presence of endothelial cells (von Willebrand and VE-cadherin); and d) inflammation (MAC387 antibody for macrophages, anti-CD45 antibody for leukocytes). Segments of all grafts can also undergo SEM for morphological assessment of any platelet or white cell adhesion/activation and the presence/absence of endothelial cells and POC.

Histomorphometric Analysis:

To quantify the degree of neointimal hyperplasia, each anastomosis can be sectioned in entirety and 5 equally-spaced sections throughout each anastomosis can be assessed to quantify neointimal hyperplasia. Each section can be imaged and neointimal area, medial area, luminal area, and circumference can be measured using ImageJ software (NIH). To quantify cellular proliferation, inflammation, and endothelialization, nuclei of positively staining cells can be counted in four different high power fields per section. Since macrophages appear mostly at the lumen/graft interface, the interface can be taken as the reference point. The interface plus 250 µm into the lumen and 250 µm into the graft's wall can define the area of interest. All the evaluations can be performed in a blinded manner to maintain an objective interpretation of the results. The data obtained from the POC-based grafts and control ePTFE grafts placed in each pig can be compared to each other. Statistical comparisons can be performed using the student's t-test.

Patency:

Patency and degree of stenosis of the grafts can be assessed noninvasively via MRA or contrast angiography, and duplex ultrasonography prior to euthanasia and graft harvest.

We claim:

1. A method for reducing the occurrence of neointimal hyperplasia and/or thrombosis following implantation of a vascular implant, said method comprising, contacting a vascular implant with all-trans retinoic acid (ATRA); and implanting the vascular implant in a patient in need of thereof, wherein the vascular implant comprises a biocompatible polymeric matrix selected from the group consisting of poly (citric acid-diol), poly(glycerol-diacid), and mixtures thereof; and the vascular implant locally releases a therapeutically effective amount of ATRA sufficient to inhibit neointimal hyperplasia and/or thrombosis by diffusing from the vascular implant to a blood vessel surface adjacent to the vascular implant when implanted in the patient.

2. The method of claim 1, wherein the vascular implant is a vascular graft, a vascular stent, or a wrap, or a gel.

3. The method of claim 1, wherein the vascular implant comprises a vascular stent or graft and a wrap or gel, wherein the wrap or gel comprises the biocompatible polymeric matrix and ATRA, and wherein the wrap or gel is placed around at least a portion of the vascular stent or graft.

4. The method of claim 1, wherein the vascular implant releases ATRA at a rate of about 0.001 to 5 mg per gram of biocompatible polymeric matrix per day.

5. The method of claim 1, wherein the vascular implant comprises about 0.001 to 15 wt % ATRA with respect to the biocompatible polymeric matrix.

6. The method of claim 1, wherein the therapeutically effective amount of ATRA is released for a period of about 1 day to about 12 weeks.

7. The method of claim 1, wherein the biocompatible polymeric matrix is elastomeric or a gel.

8. The method of claim 1, wherein microparticles or nanoparticles comprise the ATRA, wherein the microparticles or nanoparticles are embedded within the biocompatible polymeric matrix.

9. The method of claim 1, wherein the ATRA is encapsulated in micelles or liposomes, wherein the micelles or liposomes are embedded within the biocompatible polymeric matrix.

10. The method of claim 1, wherein the ATRA is absorbed within the biocompatible polymeric matrix.

11. The method of claim 1, wherein the ATRA is suspended within or dissolved within the biocompatible polymeric matrix.

12. A method for preparing a modified vascular implant, comprising providing a vascular implant; and contacting the vascular implant with all-trans retinoic acid (ATRA) to yield a modified vascular implant, wherein the modified vascular implant comprises a biocompatible polymeric matrix selected from the group consisting of poly(citric acid-diol), poly(glycerol-diacid), and mixtures thereof; and the modified vascular implant releases a therapeutically effective amount of ATRA sufficient to inhibit neointimal hyperplasia and/or thrombosis when implanted in a patient.

13. The method of claim 12, wherein the contacting comprises coating the vascular implant with a mixture comprising a biocompatible polymer prepolymer and nanoparticles, microparticles, micelles, or liposomes comprising ATRA.

14. The method of claim 13, wherein the biocompatible polymer prepolymer is a polyester prepolymer.

15. The method of claim 12, wherein the contacting comprises soaking the vascular implant in a solution comprising ATRA.

16. The method of claim 12, wherein the contacting comprises coating the vascular implant with a biocompatible polymer prepolymer; setting the coated vascular implant; and soaking the coated vascular implant in a solution comprising ATRA.

17. The method of claim 16, wherein the solution causes the biocompatible polymeric matrix to swell.

18. The method of claim 12, wherein the contacting comprises coating the vascular implant with a mixture comprising ATRA and the biocompatible polymeric matrix, wherein the biocompatible polymeric matrix is a biocompatible thermoplastic polymer.

* * * * *